United States Patent [19]

Khan et al.

[11] Patent Number: 5,440,026
[45] Date of Patent: Aug. 8, 1995

[54] PROCESS FOR THE PREPARATION OF SUCROSE 6-ESTERS

[75] Inventors: Riaz A. Khan, Sonning; Keith Smith, Mayals; Andrew Pelter; Jin Zhao, both of Uplands, all of England

[73] Assignee: Tate & Lyle Public Limited Co., London, England

[21] Appl. No.: 886,633

[22] Filed: May 21, 1992

[30] Foreign Application Priority Data

May 21, 1991 [GB] United Kingdom ............. 9110931

[51] Int. Cl.$^6$ ..................... C07H 13/00; C07H 1/00
[52] U.S. Cl. .................... 536/115; 536/116; 536/119; 536/120; 536/124
[58] Field of Search ............. 536/119, 115, 120, 116, 536/124

[56] References Cited

U.S. PATENT DOCUMENTS

| | | | |
|---|---|---|---|
| 1,685,220 | 9/1928 | Middleton et al. | 536/119 |
| 3,679,739 | 7/1972 | Schulz et al. | 536/119 |
| 4,889,928 | 12/1989 | Simpson | 536/119 |
| 4,980,463 | 12/1990 | Walkup et al. | 536/119 |
| 5,008,383 | 4/1991 | Bu'lock et al. | 536/4.1 |

OTHER PUBLICATIONS

American Chemical Society Series, 386, Chapter 3, published 1989, Bouchra et al, "New Method of Ortho-esterification Under Kinetic Control" pp. 47–63.

*Primary Examiner*—Michael G. Wityshyn
*Assistant Examiner*—Everett White
*Attorney, Agent, or Firm*—Ostrolenk, Faber, Gerb & Soffen

[57] ABSTRACT

A method for the preparation of a sucrose 6-ester comprises:

(i) reacting sucrose with a ketene acetal in the presence of an acid catalyst in an inert organic solvent to form a sucrose alkyl 4, 6-orthoester;

(ii) subjecting the sucrose alkyl 4, 6-orthoester to mild acidic hydrolysis to provide a mixture of 4- and 6-monoesters of sucrose; and (iii) treating the mixture of sucrose monoesters with a base to convert the sucrose 4-ester into sucrose 6-ester. Sucralose may be prepared by chlorination of sucrose 6-esters prepared according to the invention.

18 Claims, No Drawings

PROCESS FOR THE PREPARATION OF SUCROSE 6-ESTERS

This invention relates to an improved process for the preparation of sucrose 6-esters, which are key intermediates in one route to the production of sucralose (1, 6-dichloro- 1, 6-dideoxy-β-D-fructofuranosyl 4-chloro-4-deoxy-α-D-galactopyranoside), a high intensity sweetener having a sweetness of several hundred times that of sucrose which is disclosed in British Patent No. 1,543,167.

The preparation of sucralose involves the introduction of chlorine atoms into the 1'- and 6'- positions (i.e. displacement of two of the three primary hydroxyl groups) and at the 4-position (i.e. displacement of a secondary hydroxyl group). The third primary hydroxyl group, at the 6-position, must remain unaffected.

One important route to sucralose involves the preparation and subsequent chlorination of 2, 3, 6, 3', 4'-penta-O-acetyl sucrose in which the three hydroxyl groups to be displaced by chlorine atoms are unprotected while all the other groups are protected (see, for example, U.S. Pat. No. 4,362,869 and European Patent specification No. 31651B).

An alternative, simpler route involves the preparation of a sucrose 6-ester which can be selectively chlorinated at the 4-, 1'- and 6'-positions, under the appropriate conditions. One such method of preparing sucrose 6-esters and converting them to sucralose is disclosed in UK Patent GB 2079749B, but this method produces a mixture of acylated sucrose derivatives, with a major proportion of the 6-ester.

A more selective method of preparing sucrose 6-esters, disclosed in UK Patent Application GB 2195632A, is based upon the preparation of a sucrose 4, 6-orthoester, followed by its hydrolysis to provide a mixture of sucrose 4- and 6-esters, which are then isomerised to provide a high yield of the required 6-ester. The sucrose 4, 6-orthoester can be prepared by reacting sucrose with a trialkyl orthester in the presence of an acid catalyst in an inert organic solvent.

The present invention is based on the discovery of a new route to the preparation of sucrose 4, 6-orthoesters by direct reaction of sucrose with a suitable ketene acetal. For example, reaction of sucrose with 1, 1-dimethoxyethene in the presence of a catalyst such as p-toluenesulphonic acid or pyridinium chloride provides sucrose methyl 4, 6-orthoacetate in high yield. Other ketene acetals of interest include ketene diethyl acetal.

The use of 1, 1-dimethoxyethene to prepare methoxyethylidene derivatives of certain carbohydrates is described by Mohamed Bouchra, Pierre Calinaud and Jacques Gelas in American Chemical Society Symposium Series, 386 (1989), 54–63. Treatment of methyl α-D-glucopyranoside in dry N, N-dimethylformamide with twice the stoichiometric amount of 1, 1-dimethoxyethene and a catalytic amount of p-toluene sulphonic acid yielded methyl 4, 6-0-methoxyethylidene-α-D-glucopyranoside. The same method was used to prepare the corresponding 4, 6-orthoesters of D-glucose and D-mannose, but when the method was applied to the disaccharide, trehalose, the symmetrical 4, 6-diorthoester was obtained.

We have now found that treatment of sucrose with 1, 1-dimethoxyethene in dimethylformamide in the presence of a catalytic amount of p-toluene sulphonic acid provides 4,6-0-(1-methoxyethylidene) sucrose (sucrose methyl 4, 6-orthoacetate) in near quantitive yield. This reagent has a lower molecular weight than trimethyl orthoacetate (70 versus 120) so that less reagent can be used. Also, only one mole of methanol is released in the reaction, against two moles for trimethyl orthoacetate, so that the equilibrium is favourably displaced and a better yield is possible.

Mild acidic hydrolysis of the sucrose methyl 4, 6-orthoacetate affords a mixture of sucrose 4-acetate and sucrose 6-acetate, which can be treated with an organic base such as t-butylamine or a water soluble base such as potassium carbonate, sodium carbonate or calcium hydroxide, to convert the sucrose 4-acetate into sucrose 6-acetate. The mild acidic hydrolysis can be effected in aqueous solution or in an inert polar organic solvent containing water in an excess over the amount theoretically required (typically 3 to 10 molar equivalents based on the sucrose ester), as described in GB 2195632A.

According to the present invention, there is provided a method for the preparation of a sucrose 6-ester comprising: (i) reacting sucrose with a ketene acetal in the presence of an acid catalyst in an inert organic solvent to form a sucrose alkyl 4, 6-orthoester; (ii) subjecting the sucrose alkyl 4, 6-orthoester to mild acidic hydrolysis to provide a mixture of 4- and 6monoesters of sucrose; and (iii) treating the mixture of sucrose monoesters with a base to convert the sucrose 4-ester into sucrose 6-ester. In general, the amount of ketene acetal used in the reaction can vary from about 1 mole equivalent (ME) to about 2 ME per ME of sucrose.

The reaction between sucrose and the ketene acetal can be catalysed by passing a solution of the reactants in an inert organic solvent such as DMF through an acidic ion exchange resin, as described in British Patent Application No. 9110821.7. Macroreticular acid ion exchange resins are particularly favoured. Furthermore, as is also described in British Patent Application No. 9110821.7, the mild acid hydrolysis of the sucrose alkyl 4, 6-orthoester can also be effected by passing an aqueous solution of the sucrose alkyl 4, 6-orthoester through an acidic ion exchange resin.

The method of the present invention provides a selective route to the preparation of sucrose 6-esters and, since these can be selectively chlorinated at the 4-, 1'- and 6'- positions, it also provides a route to the preparation of sucralose. Thus, according to the present invention, there is also provided a method for the preparation of sucralose comprising: (i) reacting sucrose with a ketene acetal in the presence of an acid catalyst in an inert organic solvent to form a sucrose alkyl 4,6-orthoester; (ii) subjecting the sucrose alkyl 4, 6-orthoester to mild acidic hydrolysis to provide a mixture of 4- and 6-monoesters of sucrose; (iii) treating the mixture of sucrose monoesters with a base to convert the sucrose 4-ester into sucrose 6-ester; (iv) reacting the sucrose 6-ester with a chlorinating agent capable of effecting selective chlorination at the 4-, 1'- and 6'- positions; (v) optionally peresterifying the sucralose 6-ester so formed; and (vi) deesterifying the sucralose ester before or after separation from the reaction mixture and recovering sucralose.

The chlorination step can be effected with any of the suitable chlorinating systems, for example those disclosed in GB 2 079 749B using a reagent of the Vilsmeier type, a triarylphosphine or triarylphosphite, or sulphuryl chloride. Other useful chlorinating systems include: thionyl chloride in the presence of triphenyl phosphine oxide (GB 2 182 039A) and thionyl chloride and pyridine (GB 2 222 827A).

The invention is further illustrated by the following Examples.

EXAMPLE 1

A solution of sucrose (1.0 g; 2.9 mmol) in N, N-dimethylformamide (DMF, 10 ml ) was treated with 1, 1-dimethoxyethene (0.3 ml; 2.9 mmol) in the presence of dry p-toluene sulphonic acid (8 mg) and 5A molecular sieve (50 mg), under nitrogen at 0° C. for 80 minutes. Thin layer chromatography (Tlc) on silica using ethyl acetate: acetone: water 8:8:1 as solvent showed a fast moving major spot and two slower moving minor spots which corresponded to the sucrose 6-acetate and sucrose standards. The reaction was stopped by adding water (1 ml) and the solution was concentrated by codistillation with toluene to give a syrup.

The residue was eluted through a column of silica gel using 1–2% aqueous acetone to give 0.52 g of the fast moving product (fraction 1) and 0.24 g of the sucrose monoacetate component (fraction 2). A sample of fraction 1 was acetylated by the conventional method using acetic anhydride in pyridine. The $^1$H-nmr spectrum of the acetylated product confirmed that it was 4, 6-0-(1-methoxyethylidene) sucrose hexaacetate. The mass spectrum of the hexaacetate was also consistent with the structure ($M^{30}$—$OCH_3$=619).

Fraction 1 decomposed on storage to give, according to Tlc (as above), a mixture of sucrose methyl 4, 6-orthoacetate and sucrose monoacetate.

Fractions 1 and 2 were combined and treated with 60% aqueous acetic acid at room temperature for 2 days. Tlc (as above) revealed a single spot, indicating that the sucrose methyl 4, 6-orthoacetate had completely broken down into its monoacetate components. The solution was concentrated to a syrup and analysed by the deuterio-NMR technique, which provides unambiguous characterisation of the number and position of the acetate groups in partially acetylated sucrose derivatives. A sample of the syrup (20 mg) was treated with deuterioacetic anhydride (0.5 ml ) and deuteriopyridine (1 ml ) at 40° for 4 hours, then was concentrated and taken up in a mixture of pyridine-$d_5$ and deuteriobenzene (1:1) for determination of the 250 Mhz $^1$H-nmr spectrum. This revealed two acetate peaks at $\epsilon$1.9404 and $\epsilon$2.0666, corresponding to sucrose 4-acetate and sucrose 6-acetate, respectively. The rest of the spectrum due to ring protons was identical to that of sucrose octaacetate.

A portion of the syrup obtained above (0.2 g) was treated with toluene p-sulphonic acid (5 mg) and a drop of water in DMF at room temperature for 2 hours, then t-butylamine (1 ml) was added and the solution was stirred overnight. Tlc (as above) showed a single spot corresponding to the standard sucrose 6-acetate. The solution was concentrated to a syrup under vacuum and the structure of the product was confirmed by the deuterio-NMR technique as described above. The 250 MHz $^1$H-nmr spectrum revealed a single acetate peak corresponding to that of the standard sucrose 6-acetate. The rest of the spectrum due to ring protons was identical to that of sucrose octaacetate. The molar yield of sucrose 6-acetate was estimated as 66%, based on sucrose.

EXAMPLE 2

A solution of sucrose (1.0 g; 2.9 mmol) in DMF (10 ml) was treated with 1, 1-dimethoxyethene (0.6 ml; 5.8 mmol) in the presence of p-toluene sulphonic acid (5 mg) and 5A molecular sieve (50 mg), under nitrogen at 0° for 80 minutes. Tlc on silica using ethyl acetate: acetone: water 8:8:1 as solvent showed a fast moving major spot and two slower moving minor spots which corresponded with those of the standards, sucrose 6-acetate and sucrose.

The reaction was stopped by adding water (1 ml) and the solution was concentrated by codistillation with toluene to give a syrup. The residue was eluted through a column of silica gel with 1–2% aqueous acetone to separate the products. During this process about 50% of the sucrose methyl 4, 6-orthoacetate was broken down into its monoacetate components. The fraction containing mainly sucrose methyl 4, 6-orthoacetate (0.22 g) was treated for two hours with p-toluene sulphonic acid (5 mg) and a drop of water in DMF at room temperature, then t-butylamine (1 ml) was added and the solution was stirred overnight. Tlc (as above) gave a single spot corresponding to the standard sucrose 6-acetate. The monoacetate component was separated by elution from a silica gel column with 1–2% aqueous acetone, concentrated to a syrup and analysed by the deuterio-NMR technique as described above. The 250 MHz $^1$H-nmr spectrum revealed a single acetate peak corresponding to that of the standard sucrose 6-acetate. The rest of the spectrum due to ring protons was identical to that of sucrose octaacetate. The molar yield of sucrose 6-acetate was estimated as 85%, based on sucrose.

We claim:
1. A method for the preparation of a sucrose 6-ester comprising:
  (i) reacting sucrose with a ketene acetal in the presence of an acid catalyst in an inert organic solvent to form a sucrose alkyl 4, 6-orthoester;
  (ii) subjecting the sucrose alkyl 4, 6-orthoester to mild acidic hydrolysis to provide a mixture of 4- and 6-monoesters of sucrose; and
  (iii) treating the mixture of sucrose monoesters with a base to convert the sucrose 4-monoester into sucrose 6-monoester.
2. The method of claim 1, in which the amount of ketene acetal used in step (i) is from about 1 mole equivalent (1 ME) to 2 ME per ME of sucrose.
3. The method of claim 1, in which the ketene acetal is 1,1-dimethoxyethene.
4. The method of claim 1, in which the acid catalyst used in step (i) is chosen from the group consisting of p-toluene sulphonic acid and pyridinium chloride.
5. The method of claim 1, in which the mild acidic hydrolysis of step (ii) is effected in a medium selected from the group consisting of an aqueous solution and a solution in an inert polar organic solvent.
6. The method of claim 1, in which the base used in step (iii) to treat the mixture of sucrose 4- and 6monoesters produced in step (ii) to convert sucrose 4-monoester into sucrose 6-monoester is an organic base or a water soluble base.
7. The method of claim 6, in which the amount of ketene acetal used in step (i) is from about 1 mole equivalent (1 ME) to 2 ME per ME of sucrose, the acid catalyst used in step (i) is chosen from the group consisting of p-toluene sulphonic acid and pyridinium chloride, and the mild acidic hydrolysis of step (ii) is effected in a medium selected from the group consisting of an aqueous solution and a solution in an inert polar organic solvent containing water in excess.

8. The method of claim 7, in which the ketene acetal is 1,1-dimethoxyethene.

9. A method for the preparation of sucralose comprising:
   (i) reacting sucrose with a ketene acetal in the presence of an acid catalyst in an inert organic solvent to form a sucrose alkyl 4, 6-orthoester;
   (ii) subjecting the sucrose alkyl 4, 6-orthoester to mild acidic hydrolysis to provide a mixture of 4- and 6-monoesters of sucrose;
   (iii) treating the mixture of sucrose monoesters with a base to convert the sucrose 4-monoester into sucrose 6-monoester;
   (iv) reacting the sucrose 6-monoester with a chlorinating agent capable of effecting selective chlorination at the 4-, 1'- and 6'- positions; and (v) deesterifying the sucralose ester so formed before or after separation from the reaction mixture and recovering sucralose.

10. The method of claim 9, in which the amount of ketene acetal used in step (i) is from about 1 mole equivalent (1 ME) to 2 ME per ME of sucrose.

11. The method of claim 9, in which the acid catalyst used in step (i) is chosen from the group consisting of p-toluene sulphonic acid and pyridinium chloride.

12. The method of claim 9, in which the mild acidic hydrolysis of step (ii) is effected in a medium selected from the group consisting of an aqueous solution and a solution in an inert polar organic solvent containing water in excess.

13. The method of claim 9, in which the base used in step (iii) to treat the mixture of sucrose 4- and 6-monoesters produced in step (ii) to convert sucrose 4-monoester into sucrose 6-monoester is an organic base or a water soluble base.

14. The method of claim 13, in which the sucralose ester is peresterified after chlorination and before deesterification.

15. The method of claim 14, in which the amount of ketene acetal used in step (i) is from about 1 mole equivalent (1 ME) to 2 ME per ME of sucrose, the acid catalyst used in step (i) is chosen from the group consisting of p-toluene sulphonic acid and pyridinium chloride, and the mild acidic hydrolysis of step (ii) is effected in a medium selected from the group consisting of an aqueous solution and a solution in an inert polar organic solvent containing water in excess.

16. The method of claim 15, in which the ketene acetal is 1,1-dimethoxyethene.

17. The method of claim 9, in which the sucralose ester is peresterified after chlorination and before deesterification.

18. The method of claim 17, in which the ketene acetal is 1,1-dimethoxyethene.

* * * * *